(12) United States Patent
Yang et al.

(10) Patent No.: US 10,241,258 B2
(45) Date of Patent: Mar. 26, 2019

(54) FLEXIBLE BIODEGRADABLE POLYMERIC STEP-INDEX OPTICAL FIBER

(71) Applicant: The Penn State Research Foundation, University Park, PA (US)

(72) Inventors: Jian Yang, State College, PA (US); Zhiwen Liu, State College, PA (US); Dingying Shan, State College, PA (US); Chenji Zhang, San Jose, CA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 15/956,483

(22) Filed: Apr. 18, 2018

(65) Prior Publication Data

US 2018/0299612 A1 Oct. 18, 2018

Related U.S. Application Data

(60) Provisional application No. 62/486,711, filed on Apr. 18, 2017.

(51) Int. Cl.
*G02B 6/02* (2006.01)
*G02B 6/036* (2006.01)
(Continued)

(52) U.S. Cl.
CPC .... *G02B 6/02033* (2013.01); *B29D 11/00663* (2013.01); *C08G 63/16* (2013.01);
(Continued)

(58) Field of Classification Search
CPC ............ G02B 6/02033; G02B 6/03638; G02B 6/02042; C08G 2230/00; C08G 63/06;
(Continued)

(56) References Cited

U.S. PATENT DOCUMENTS 8,574,311 B2 11/2013 Yang et al.
2008/0255677 A1* 10/2008 Libera ................. A61F 2/30767
623/23.57

(Continued)

FOREIGN PATENT DOCUMENTS

WO 2001085637 A2 11/2001

OTHER PUBLICATIONS

Choi et al., Step-index optical fiber made of biocompatible hydrogels, Adv. Mater. 27 (2015). 4081e4086.*
(Continued)

*Primary Examiner* — Michael Mooney
(74) *Attorney, Agent, or Firm* — Douglas Wathen

(57) ABSTRACT

A biocompatible and biodegradable polymeric step-index optical fiber includes a core and a cladding around the core. The core is made from a core material fabricated by bonding a citric acid and at least a first monomer using a synthesis process. The cladding is made from a cladding material fabricated by bonding the citric acid and at least a second monomer using the synthesis process. The core has a refractive index higher than that of the cladding, while a difference between an initial modulus of the core and the cladding is preferably less than 30% and a difference between the biodegradation rates of the core and cladding is preferably less than 30% after about 4 weeks. Optical properties of the core and cladding are tunable by adjusting monomer ratios, choices of monomers or cross-linking degrees.

19 Claims, 13 Drawing Sheets

(51) Int. Cl.
  *B29D 11/00* (2006.01)
  *C08G 63/16* (2006.01)
  *C08G 63/52* (2006.01)

(52) U.S. Cl.
  CPC ......... *C08G 63/52* (2013.01); *G02B 6/03638* (2013.01); *C08G 2230/00* (2013.01); *G02B 6/02042* (2013.01)

(58) Field of Classification Search
  CPC ........ C08G 63/16; C08G 63/52; C08G 63/66; C08G 63/685; C08G 63/914; C08G 63/6858; A61N 5/0601; A61N 2005/0602; A61N 2005/063; A61N 2005/0662; A61L 27/18
  USPC .......................... 385/123–128, 141, 143, 145
  See application file for complete search history.

(56) References Cited

U.S. PATENT DOCUMENTS

2009/0325859 A1    12/2009    Ameer et al.
2016/0245990 A1    8/2016    Boyden et al.

OTHER PUBLICATIONS

Gyawali et al., Citric-acid-derived photo-cross-linked biodegradable elastomers, J. Biomater. Sci. Polym.Ed. (2010) 1761e1782.*

* cited by examiner

FLEXIBLE BIODEGRADABLE POLYMERIC STEP-INDEX OPTICAL FIBER

REFERENCE TO RELATED PATENT APPLICATIONS

The present invention claims priority from U.S. Provisional Patent Application Ser. No. 62/486,711, filed Apr. 18, 2017, the entire content of which is incorporated herein by reference.

FIELD OF THE INVENTION

This invention relates to flexible biodegradable polymeric step-index optical fibers and a method of making thereof.

BACKGROUND OF THE INVENTION

A long-standing hurdle, which has greatly plagued biomedical optical technologies, is the turbidity of biological tissue. Due to significant scattering and absorption loss, light cannot be efficaciously delivered to or collected from target regions within deep tissue, significantly hindering the capability to monitor post-surgical healing of tissues or organs, perform highly targeted light-based therapy, or optogenetic stimulation, to name but a few examples. Implanting fibrous optical waveguide in tissues or organs for light delivery or collection is one of the most effective methods for alleviating this problem. However, traditional silica fibers are not only non-degradable, but also fragile and brittle in nature, thus presenting a significant limitation as an implantable device. Waveguides made from single traditional materials, such as poly(ethylene glycol) (PEG), silk, agarose gel, and poly(L-lactic acid) (PLA) have also been reported. However, due to the lack of an intrinsic cladding layer, single material waveguides tend to have high loss, resulting from significant interaction of the guided optical wave with the surrounding medium (such as tissues in vivo). To address this issue, a biocompatible step-index fiber optical waveguide consisting of a PEG core and an alginate hydrogel cladding was developed for organ-scale light delivery and collection. Later, fibers having a step-index structure but made of alginate-polyacrylamide hydrogel and silk were also demonstrated. Despite the progress, hitherto the underlying materials either suffer from non-degradability or have limited processability and designability. In general, a fundamental challenge of the field is the lack of a suitable material platform that can simultaneously meet the diversified requirements on optical (tailored refractive indices for both the core and the cladding, low optical loss), mechanical (tunable mechanical flexibility for tissue compliance), and biological (biocompatibility and programmable biodegradability) functionalities.

SUMMARY OF THE INVENTION

Citrate-based materials are a group of designable biodegradable elastomers that can be completely degraded in the body and have demonstrated their safety in various animal models. Specifically, the use of the citrate platform polymers enables ultra-fine tuning of a refractive index difference (~$10^{-3}$) between the core and the cladding layers while maintaining virtually the same polymer backbone and thus achieving seamless integration of both layers with matched mechanical characteristics and a homogenous biodegradation rate to yield high device integrity. The present approach uses a single citrate based material platform, which utilize a core and cladding material with matched mechanical and biological properties such that the light field is not exposed to surrounding tissue resulting in low loss and the fiber is not prone to mechanical deformation and non-uniform degradation.

The present invention provides a biocompatible and biodegradable polymeric step-index optical fiber, including a core and a cladding surrounding the core. The core is made from a core material, which may be fabricated by bonding a citric acid and at least a first monomer using a synthesis process. The cladding is made from a cladding material which may be fabricated by bonding the citric acid and at least a second monomer using the synthesis process. Both the core material and the cladding material are citric acid based, but may have at least one monomer different from each other.

Optical properties, mechanical properties and biodegradation rates of the core and cladding may be tuned by adjusting monomer ratios, choices of monomers or cross-linking degrees such that the core material and the cladding material may have different refractive index and compliant mechanical properties and biodegradation rate. The examples of the mechanical properties are an initial modulus and tensile strength. Optical properties include the refractive index, optical loss, optical gain, light absorption and light emission.

In one embodiment, the core has a refractive index higher than that of the cladding, where a difference between an initial modulus of the core and the cladding is less than 30% and a difference between the biodegradation rates of the core and cladding is less than 30% after about 4 weeks.

In another embodiment, the core material further includes a third monomer and the cladding material further includes a fourth monomer, and wherein the fourth monomer is different from the first, second and third monomers.

The synthesis process may be by reacting the citric acid with diols and/or amino acids via a facile polycondensation reaction.

The refractive index difference between the core and cladding may be in the range of $10^{-3}$ to $10^{-1}$.

The initial modulus of the core and cladding may be in the ranges of $10^{-1}$ to $10^{2}$ MPa.

The core and/or cladding may provide adhesive or fluorescent properties through conjugating the polymer of the respective core and/or cladding with functional chemicals, biological molecules or drugs.

In one embodiment, the cladding is poly(octamethylene citrate) (POC) and the core is poly(octamethylene maleate citrate) (POMC).

A POC pre-polymer may be prepared by adding citric acid and 1,8-octanediol (OD) with a molar ratio and a POMC pre-polymer may be prepared with a mixture of the citric acid, maleic anhydrate, and OD with a molar ratio by replacing part of the citric acid with the maleic anhydrate during the synthesis process.

In one version, the molar ratio of the citric acid and OD is 1:1 for preparing the POC pre-polymer and the molar ratio of the citric acid, maleic anhydrate and OD is 0.4:0.6:1 for preparing the POMC pre-polymer.

In another embodiment, the biocompatible and biodegradable polymeric step-index optical fiber may include one hollow channel. The hollow channel may be for a microfluidic channel incorporated for delivery or collection of liquids.

In another embodiment, the biocompatible and biodegradable polymeric step-index optical fiber may have more than one core.

In yet another embodiment, the biocompatible and biodegradable polymeric step-index optical fiber may have more than one cladding layer.

The present invention shows the proof of concept of using the citrate-based fiber for image transmission, which indicates the tantalizing potential for implantation inside a human body for an extended period of time to allow long-term monitoring and imaging. The obtained optical waveguides have great potential in biomedical applications including tissue regeneration, drug delivery, light-based therapy, optogenetic stimulation, bio-imaging, and sensing.

DETAILED DESCRIPTION OF THE INVENTION

Overview

Figure 1A:
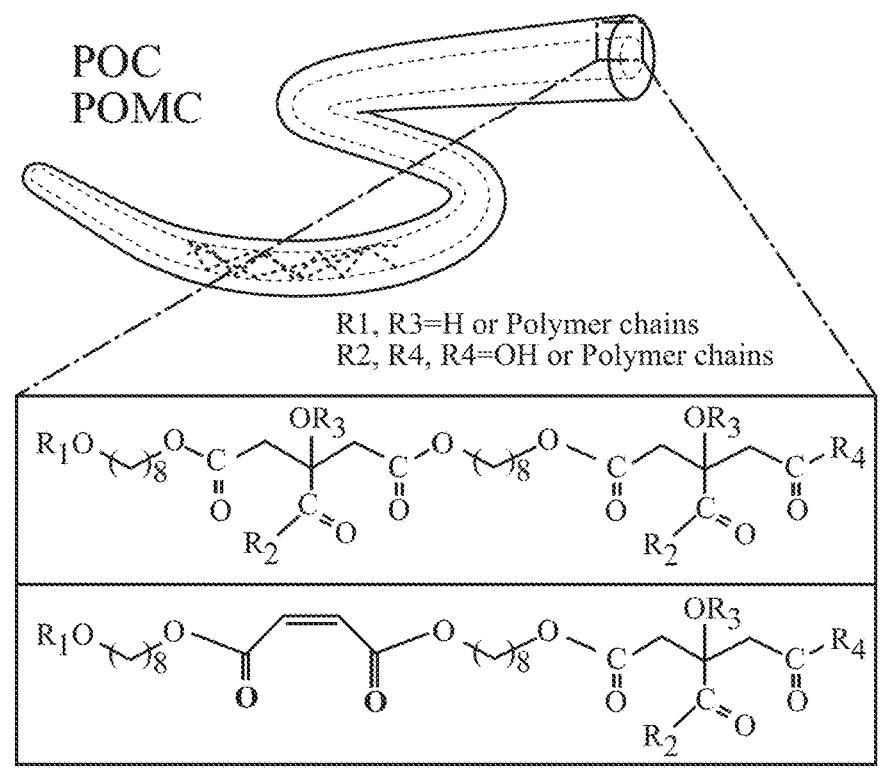
FIG. 1A is a schematic illustration of a flexible core/cladding step-index optical fiber and the chemical structures of the core (POMC) and cladding (POC) materials.

The present invention provides a citrate-based polymeric step-index optical fiber, which is flexible, biodegradable and low-loss. The citrate-based polymeric optical fiber includes a core and a cladding made from a core material and a cladding material respectively. According to an embodiment of the present invention, both the core material and cladding material are citrate-based materials. The optical properties such as refractive indices, mechanical properties such as Young's modulus, and biodegradation rates of the citrate-based materials are tunable.

The initial modulus means the modulus at a tensile strain of 10%.

In this work, we conducted two in vitro degradation studies on POC (cladding material) and POMC (core material) films: 1) in vitro accelerated degradation study in 0.05 sodium hydroxide (NaOH) solution at 37° C.; 2) in vitro degradation study in phosphate buffered saline (PBS) buffer solution at 37° C. For accelerated degradation, the main purpose is to test if a material can completely degrade and to compare degradation rates between different materials. We used this study to compare the degradation profiles of POC and POMC materials, and proved they can completely degrade and have matched degradation rate. PBS buffer is used to mimic body fluid, so PBS degradation (37° C.) is a commonly used in vitro degradation method and the results are more close to the actual degradation in vivo. It takes much longer time to do degradation study in PBS than the accelerated degradation in NaOH. We only provided the PBS degradation results of POC and POMC films for 12 weeks to compare their degradation profiles.

For the optical fiber, we conducted in vitro PBS study (37° C.) for one month.

The core material and the cladding material may be selected from a variety of citrate-based materials such that the refractive indices of the core and cladding are sufficiently different for step-index optical fiber usage, but the initial modulus and biodegradation rates of the core and cladding are sufficiently similar to each other such that the provided optical fiber is flexible and the core and cladding degrade at a similar rate.

Citrate-based materials are a group of designable biodegradable elastomers that can be completely degraded in body and have demonstrated their safety in various animal models. Citrate-based materials with high refractive indices may be developed through introducing particular groups that lead to a high refractive index, such as the imide, styrene, and xylylene groups. By introducing particular groups that lead to a low refractive index, such as fluorides, citrate-based materials with low refractive indices may be produced.

The present invention provides a methodology to design and fabricate biodegradable and biocompatible step-index optical waveguides with the citrate-based platform synthetic polymers. By applying similar synthesis processes but slightly adjusting monomer ratios, choices of monomers or crosslinking degrees, a number of similar polymers may be developed with slightly different chemical structures which provides tunable optical properties and various functionality, while maintaining similar mechanical properties, biodegradation rates, and swelling ratios.

For example, the core material may be fabricated by bonding a citric acid and a first monomer and the cladding material may be fabricated by bonding the same citric acid and a second monomer. The core material may include additional monomers. The cladding material may include additional monomers which are different from the additional monomers in the core material.

For example, if both the core and the cladding have the common monomer A, citric acid, the second monomer in core and cladding can be B or different monomers, or combination of monomers.

In another version, the core can be citrate-based polymers, the cladding can be non-citrate based polymers, vise versa.

We can vary the monomers to react with citric acid to form the core and the cladding.

The core and the cladding have a nearly identical polymer backbone so that they may have compatible mechanical properties but controllable, distinct refractive indices, and seamless integration between the core and cladding.

Tunable optical properties include but are not limited to refractive index, optical loss, absorption, and emission. Various functionalities can also be obtained through conjugating the polymer with functional chemicals, biological molecules (DNA, protein, peptide, etc.) and drugs.

In a preferred embodiment, the refractive index difference between the core and cladding materials may be tuned in the range of $10^{-3}$ to $10^{-1}$. The initial modulus of the core and cladding materials may be tuned from $10^{-1}$ to $10^2$ MPa. The degradation profiles of the core and cladding materials may be adjusted ranging from several days to more than one year. It may be said that the core and cladding materials have matched mechanical property for step-index optical fiber usage if the difference between initial modulus of the core and cladding materials is less than 30%. It may be said that the core and cladding materials have matched biodegradation profiles if the degradation rate difference between the core and cladding materials is less than 30% after four weeks.

A suitable optical material platform can enable a plethora of light-based sensing and activation applications in biology and medicine. The platform of the present invention simultaneously provides desired optical, mechanical and biological functionalities. Specifically, the optical fiber of the present invention provides tailored refractive indices for both the core and the cladding and low optical loss. The optical fiber of the present invention provides tunable mechanical flexibility for tissue compliance. The optical fiber of the present invention is biocompatible and provides programmable biodegradability.

The citrate based fiber may be functionalized or drug encapsulated.

The present invention may be used for fluorescence sensing with the use of citrate fibers to deliver light and collect fluorescence signals. The optical fiber of the present invention may be used for citrate fiber optogenetics and citrate fiber imaging.

Figure 9:
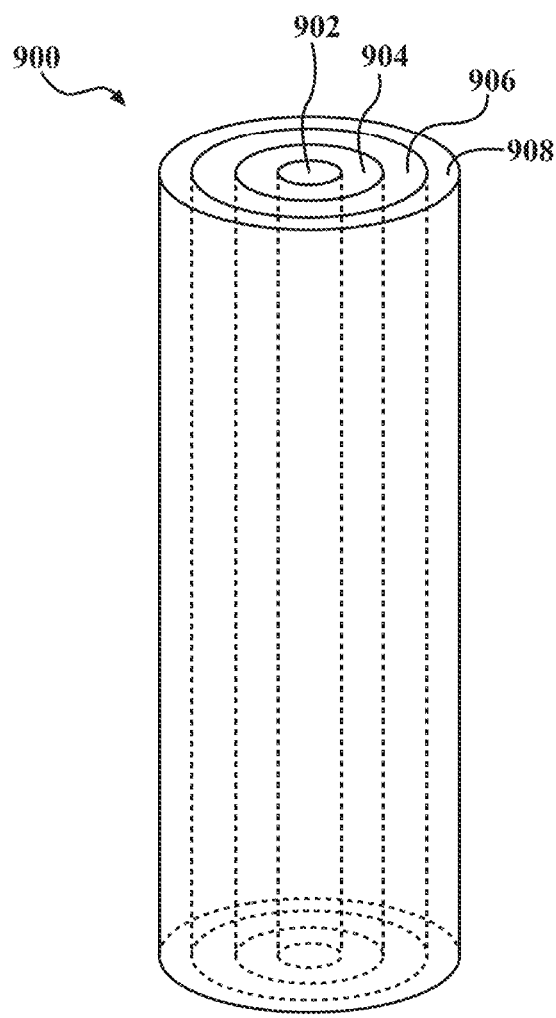
FIG. 9 is a schematic showing an embodiment having co-axial fibers.

The citrate-based fiber may include multiple step-index fibers within one "big fiber", for example, as co-axial fibers, thus within the same fiber, as shown in FIG. 9. There are both small light delivery fibers and also small light collections fibers, and may also include a drug delivery catheter along with step-index fibers within one fiber.

A two-step fabrication method is provided to achieve the core-cladding bilayer structure, including fabricating a cladding around a metal wire, followed by removing the metal wire and forming a core inside the cladding. The details of the fabrication method will be provided later. Other suitable methods may also be used.

An Example

In order to more fully explain the invention, certain specific examples will now be described, along with test results for these specific examples. The present invention is not limited to these specific examples.

The biocompatible and biodegradable step-index optical fiber is fabricated from citrate-based polymeric elastomers. Citric acid, a Krebs cycle intermediate, is the key component used in the citrate methodology, through which various crosslinkable elastomeric polymers can be synthesized by reacting the multifunctional citric acid with different diols and/or amino acids via a facile polycondensation reaction. Unlike natural materials (e.g., silk) or traditional synthetic polymers (e.g., poly lactic-co-glycolic acid (PLGA)) that usually lack tunability for key optical, mechanical, and/or degradation properties, the family of citrate-based biodegradable elastomers possesses tunable mechanical strengths (from tens of Pascal to mega Pascal), programmable degradation rates (from a few days to over a year), reactive nature between citrate-based polymers, multi-functionalities (e.g., adhesive, fluorescent), and ultrafine tuning of refractive index ($\sim 10^{-3}$), as presented in FIG. 1C.

To develop a low-loss step-index bio-optical fiber, the core material requires a higher refractive index than the cladding and yet their mechanical properties (e.g., tensile strength and modulus) should be matched, both of which can be accomplished by tailoring the chemistry of citrate-based polymers. In this example, a biodegradable and biocompatible step index optical fiber is fabricated from a group of poly (diol citrate) polymers. Specifically, two exemplary citrate-based elastomers, namely, poly(octamethylene citrate) (POC) and poly(octamethylene maleate citrate) (POMC) are used.

By applying similar synthesis processes but slightly adjusting monomer ratios, choices of monomers or crosslinking degrees, POMC and POC may have distinct optical properties but matched mechanical properties, biodegradation rates, and swelling ratios. Due to the higher refractive index of POMC than POC within a broad range of wavelength from 400 nm to 1500 nm, the step index optical fiber was fabricated by applying POMC as the core.

Synthesis of POC and POMC Pre-Polymers

To prepare a POC pre-polymer, citric acid (CA) and 1,8-octanediol (OD) with a mole ratio of 1:1 were added to a round-bottom flask, and the mixture was melted within 20 minutes by stirring the contents in the flask at 160° C. Once the constituents melted, the temperature was changed to 140° C. and the reaction was allowed to progress for an additional 1.5 hours to produce the POC pre-polymer. For the preparation of a POMC pre-polymer, CA, maleic anhydrate (MAn), and OD, with a feeding molar ratio of 0.4:0.6:1, were mixed and reacted based the same procedure as the POC pre-polymer synthesis.

Structure Characterization of POC and POMC Pre-Polymers

Figure 1B:
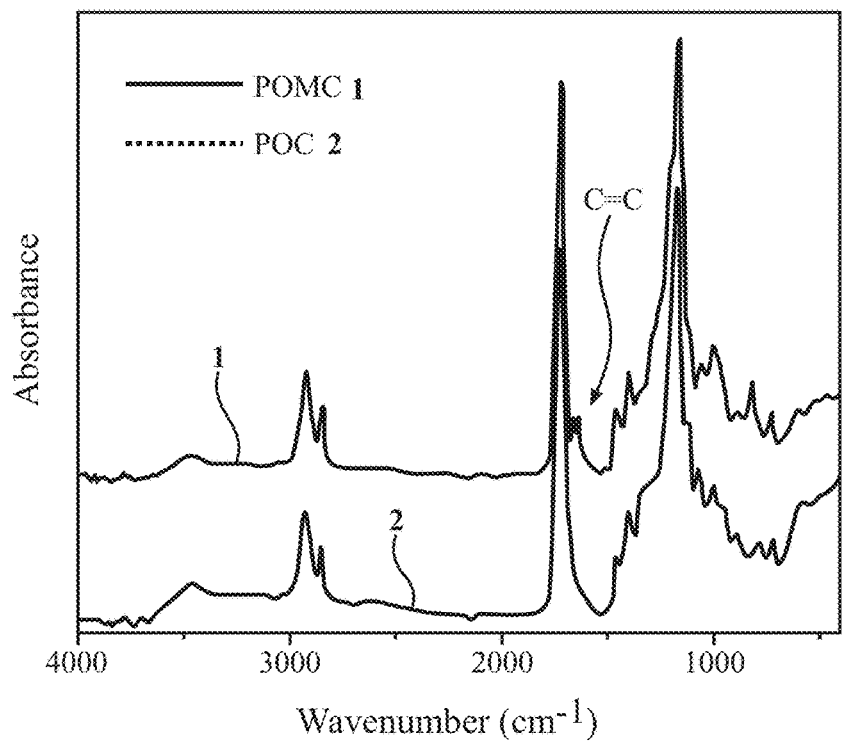
FIG. 1B is a FTIR (Fourier transform infrared spectroscopy) spectra of POMC and POC.

POC and POMC have nearly identical polymer backbones but slightly different chemical structures, as shown in FIG. 1A, arising from the presence of extra maleate groups in POMC by replacing part of the citric acid with maleic anhydrate during the synthesis process. The difference between these two polymers is supported by the appearance of a C=C stretch peak at 1643 cm$^{-1}$ of POMC in the attenuated total reflectance Fourier transform infrared (ATR-FTIR) spectra, as shown in FIG. 1B.

Optical Characterization of POC and POMC Pre-Polymers

Figure 1C:
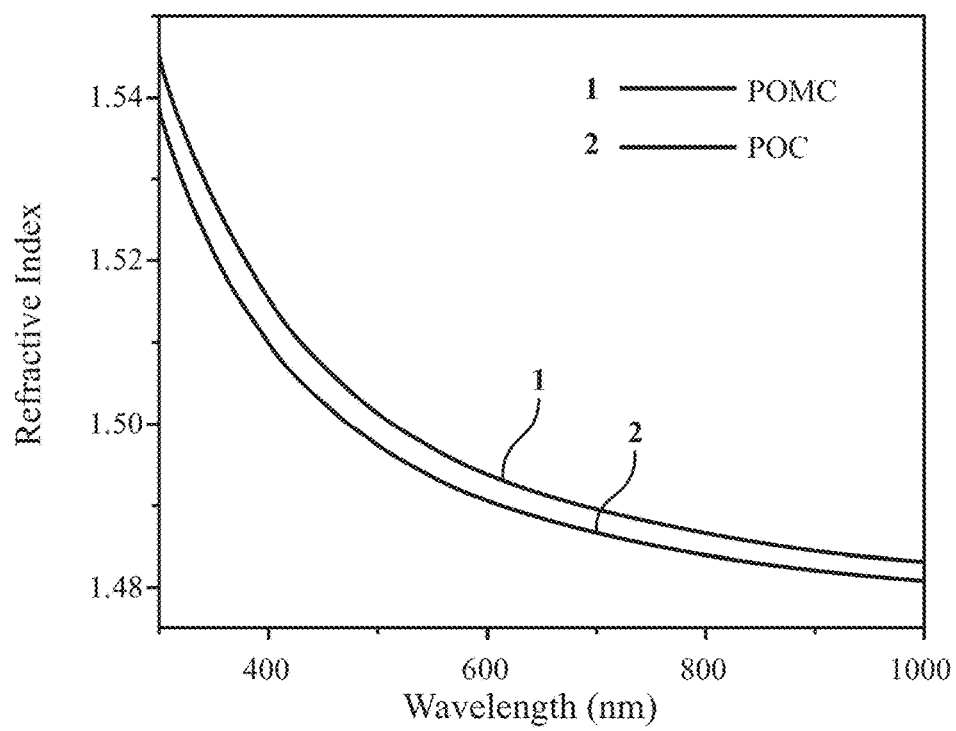
FIG. 1C is a graph showing refractive index-wavelength curves of POMC and POC.

Refractive indices of POMC and POC were measured with an ellipsometer (J A Woollam M2000-U). Testing samples were prepared by spin-coating 20% (w/v) pre-polymer solutions on a cover slip at a speed of 1000 rpm for 60 s, and then followed by a thermal crosslinking. POC was crosslinked at 70° C. for 7 days and 80° C. for 3 days, while POMC was crosslinked at 70° C. for 3 days followed by crosslinking at 80° C. for 3 more days. Five samples were tested for each material. Although there is little difference in chemical structure between POC and POMC, POMC possesses a higher refractive index than POC within a broad range of wavelength from 300 nm to 1000 nm, with an index difference of ~0.003 corresponding to a numerical aperture of approximately 0.1, as shown in FIG. 1C.

Fiber Transmission Characterization of POC and POMC Pre-Polymers

Figure 1D:
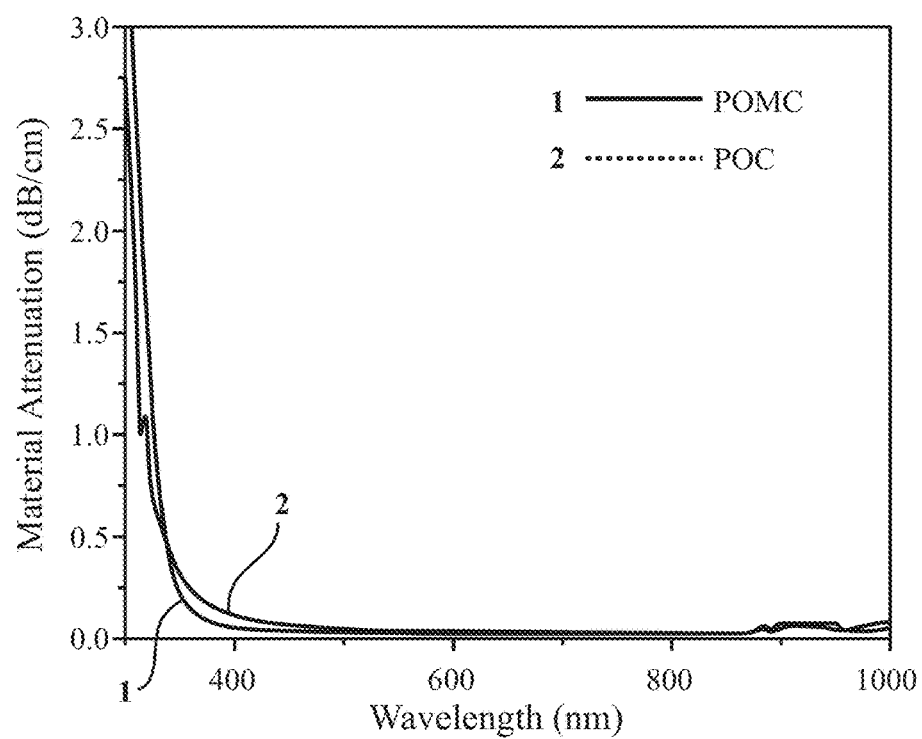
FIG. 1D is a graph showing material attenuations-wavelength curves of POMC and POC.

For the study of light absorption properties, crosslinked POC and POMC cubes inside a cuvette with a side length of 10 mm were prepared. The crosslinked cubes were then placed in a Plate Reader for test under the scanning range from 325 nm to 1000 nm to obtain the absorption results. Material attenuation presented in FIG. 1D indicates that both POC and POMC have relatively low absorption (<0.13 dB/cm) at visible and near-infrared wavelengths, which can enable large distance (e.g. organ scale) light propagation.

Mechanical Properties Characterization of POC and POMC Pre-Polymers

Figure 2A:
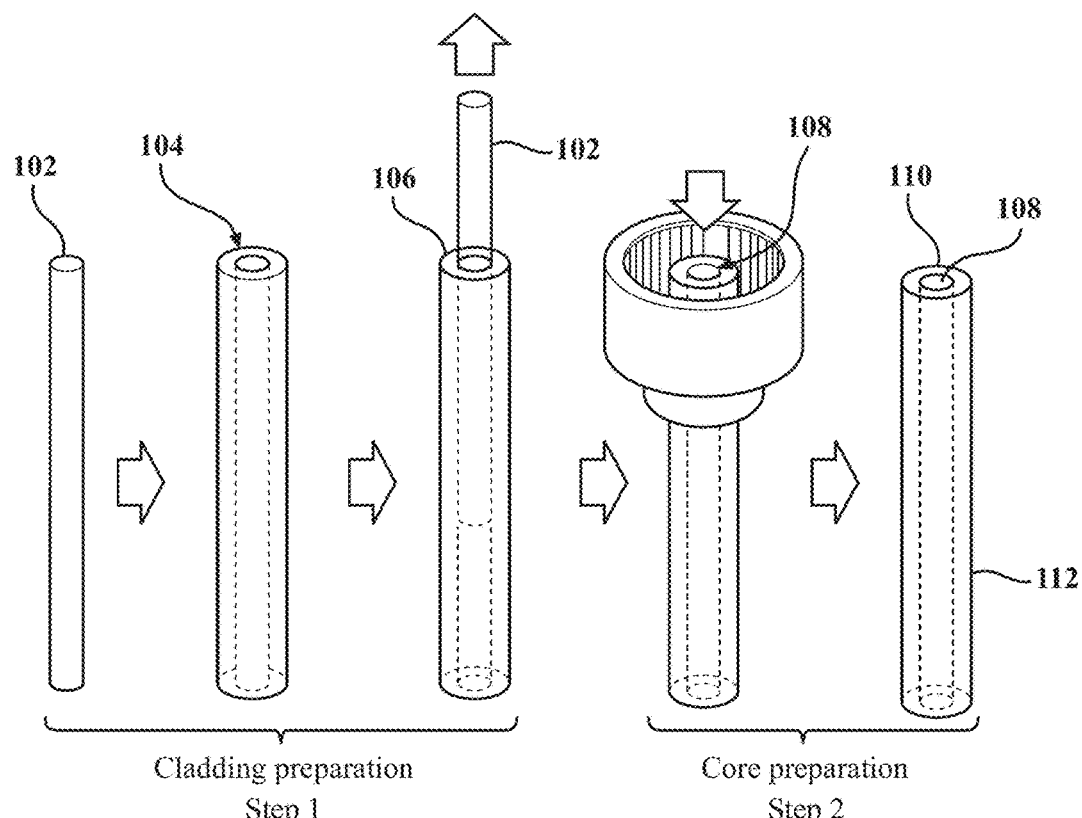
FIG. 2A is a schematic illustration of a fabrication process for the citrate-based polymeric step-index optical fiber.
Figure 2B:
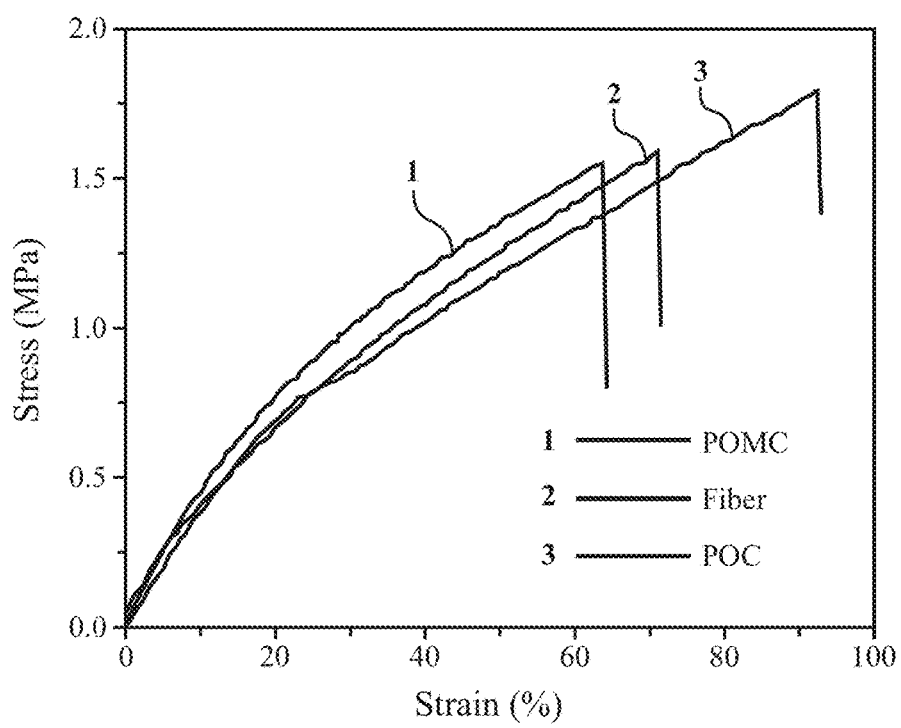
FIG. 2B is a graph showing tensile stress-strain curves of crosslinked POMC film, an optical fiber and crosslinked POC film.

Mechanical tests were conducted according to the ASTM D412a standard on an Instron 5966 machine equipped with a 500 N load cell. Tests were performed on polymer films (3 cm in length, and 0.5 cm in width) and fibers (3 cm in length) samples. Samples were pulled until failure at a rate of 100 mm/min to obtain the stress-strain curves. The initial slope (0-10%) of the curve was used to determine the initial modulus of the samples. Mechanically, POC and POMC exhibit an elastomeric nature with matched stress-strain curves under external strain of less than 20%, as indicated in FIG. 2B.

In Vitro Degradation Study

Six groups of samples were prepared for each degradation time point. The samples were weighed to find the initial mass ($W_0$), and suspended in PBS (pH 7.4) at 37° C. The PBS buffer was replaced daily in the first week and weekly in subsequent weeks to ensure a constant pH of 7.4. At the desired time point, the samples were rinsed with de-ionized water, freeze-dried and weighed to find the remaining mass ($W_t$). Six specimens were averaged, and the results are presented as means±standard deviation. The accelerated degradation was conducted in the same procedure except using 0.05 M NaOH as the degradation solution and replacing it every 4 hrs. The percent mass remaining was calculated based on the following equation:

$$\text{Mass Remaining (\%)} = \frac{W_t}{W_o} \times 100\% \qquad (1)$$

Figure 5A:
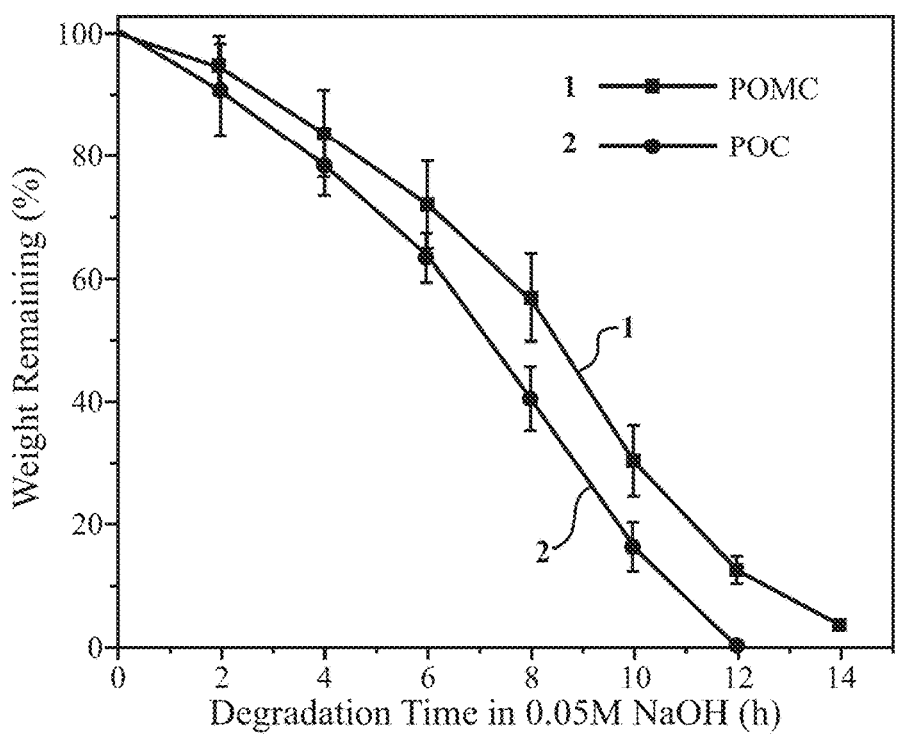
FIG. 5A is a graph showing in vitro accelerated degradation studies of crosslinked POMC and POC films in 0.05M NaOH solution.
Figure 5B:
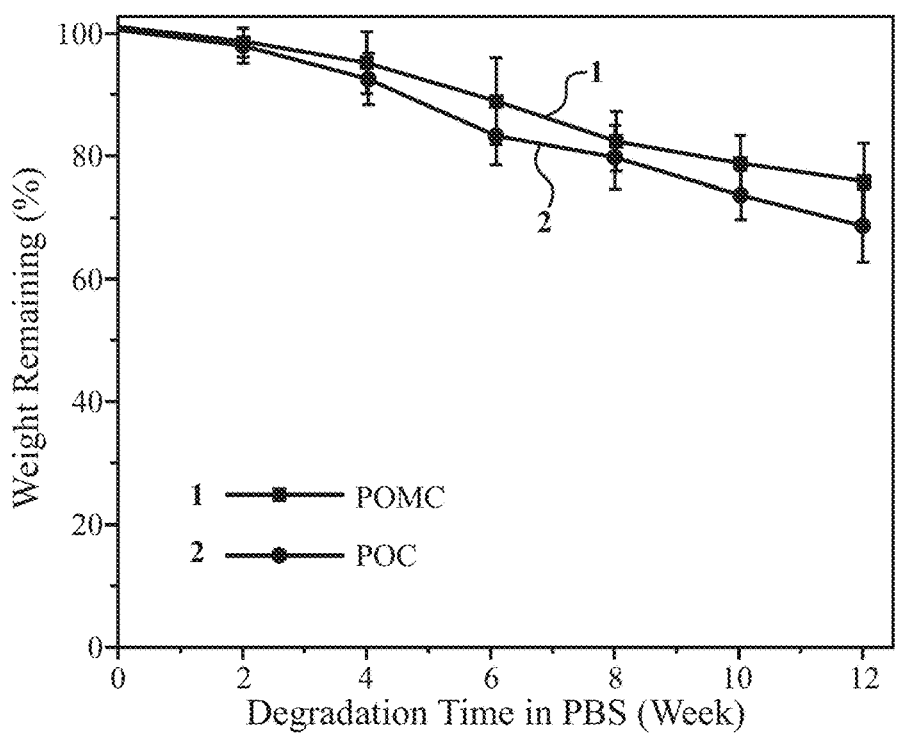
FIG. 5B is a graph showing in vitro degradation studies of crosslinked POMC and POC films in PBS (pH 7.4)

In the accelerated degradation study, POC degraded slightly faster than POMC in 0.05M NaOH solution, as shown in FIG. 5A. Under this condition, POC completely degraded in 12 hours, while POMC took 16 hours to finish the process. The degradation profiles of POC and POMC in PBS (pH 7.4) are presented in FIG. 5B. During the first 4 weeks, POC and POMC had matched degradation profiles, and there were no significant differences even after 12 weeks.

In vitro cyto-compatibility of POC and POMC degradation products and films were tested on 3T3 fibroblast cells using a well-known polymer poly lactic-co-glycolic acid (PLGA5050) used in many Food and Drug Administration (FDA)-approved medical devices as a control. The polymer films and their degradation products showed minimal cytotoxicity, shown in FIGS. 6 and 7, and the polymer films also effectively supported cell proliferation, shown in FIG. 8.

In Vitro Cell Culturing Study

The relative cytotoxicity of degradation products and films were quantitatively assessed by a Cell Counting Kit-8 (CCK-8) assay against 3T3 fibroblasts using a well-known polymer poly lactic-co-glycolic acid (PLGA5050) used in many Food and Drug Administration (FDA)-approved medical devices as a control. For the study of the cytotoxicity of degradation products, polymer films (1 g) were fully degraded in 10 mL of 2 M NaOH solution. The resultant degradation products solutions were adjusted to pH 7.4 with 1 M HCl solution and then diluted to 1×, 10× and 100× concentrations using PBS (pH 7.4). All the solutions were filtered through a sterilized 0.22 μm filter prior to cell culturing. Subsequently, 200 μL of cell suspension with the density of 5×10$^4$ cells/mL in Dulbecco's modified eagle's medium (DMEM, with 10% fetal bovine serum (FBS)) was added to each well in a 96-well plate. The culture plates were maintained in an incubator at 37° C., 5% CO2 and 95% relative humidity for 24 hrs. At the second day, 20 μL of degradation products with 1×, 10× and 100× concentrations were added to each predetermined well for cell incubation for another 24 h followed by CCK-8 assay analysis. The cell viabilities of 3T3 cells in medium containing polymer degradation solutions were normalized to that of cells cultured in normal medium. To test the cytotoxicity of polymer films, films were cut into circular discs with the diameter of 7 mm. The films were sterilized by treating with 70% ethanol (overnight), sterilized PBS (1 hr) and UV light (1 hr) in sequence. 200 μL of a cell suspension (5×10$^4$ cells/mL) in culture medium was added to each well in a 96-well plate with a film sample on the bottom. CCK-8 assay analysis was performed after 24 h to determine the cytotoxicity. For the cell proliferation study, 200 μL of a cell suspension of 5×10 cells/mL in culture medium was added to each well in a 96-well plate with polymer films. The CCK-8 assay was conducted after incubating for 1, 3, 5 and 7 days.

Figure 6:
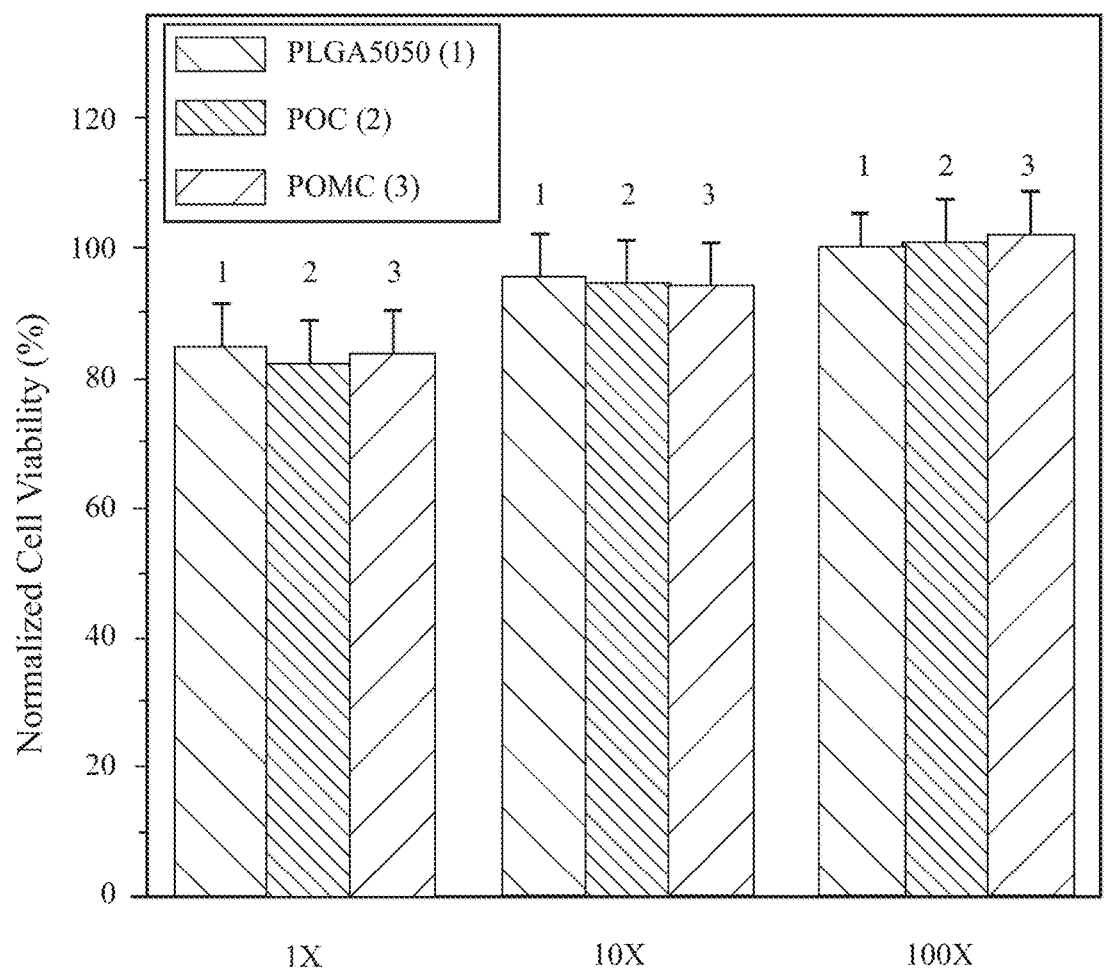
FIG. 6 is a chart showing a CCK8 assay against 3T3 fibroblast to test the cytotoxicity of degradation products of crosslinked POC and POMC films using PLGA5050 film as control.
Figure 7:
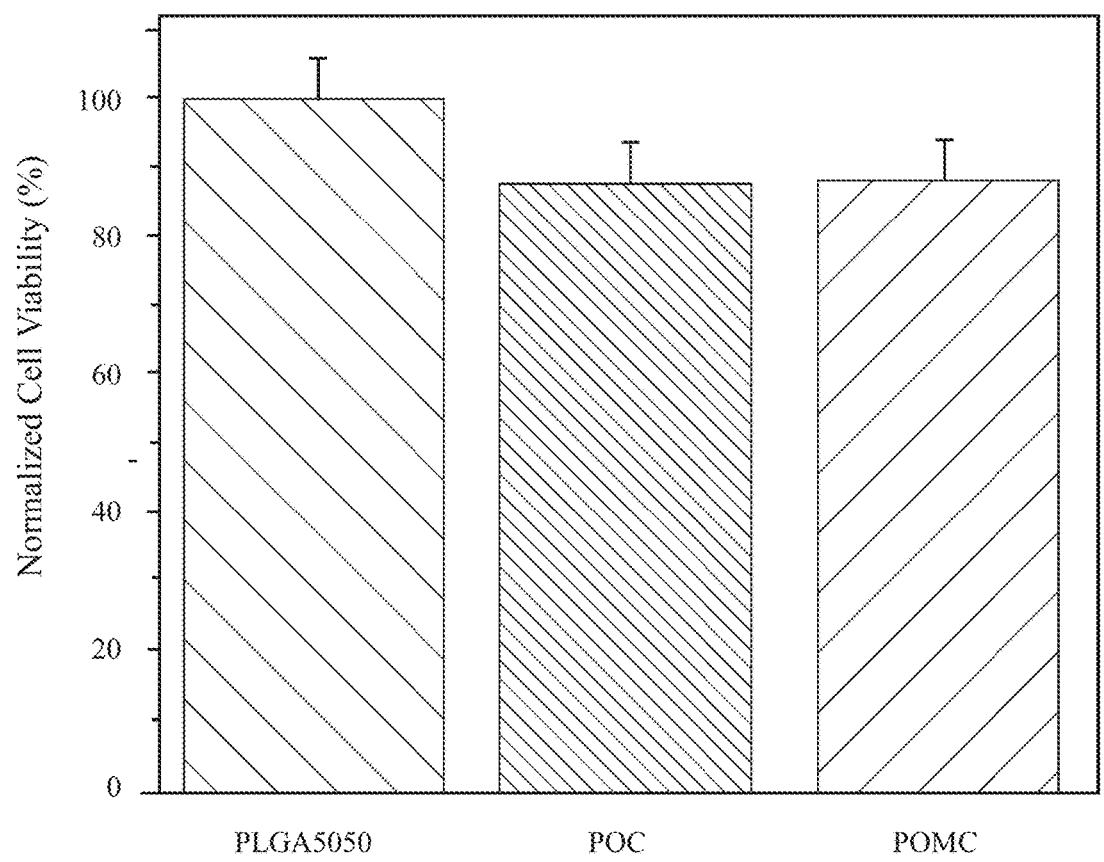
FIG. 7 is a chart showing a CCK8 assay against 3T3 fibroblast to test the cytotoxicity of crosslinked POC and POMC films using PLGA5050 film as control.
Figure 8:
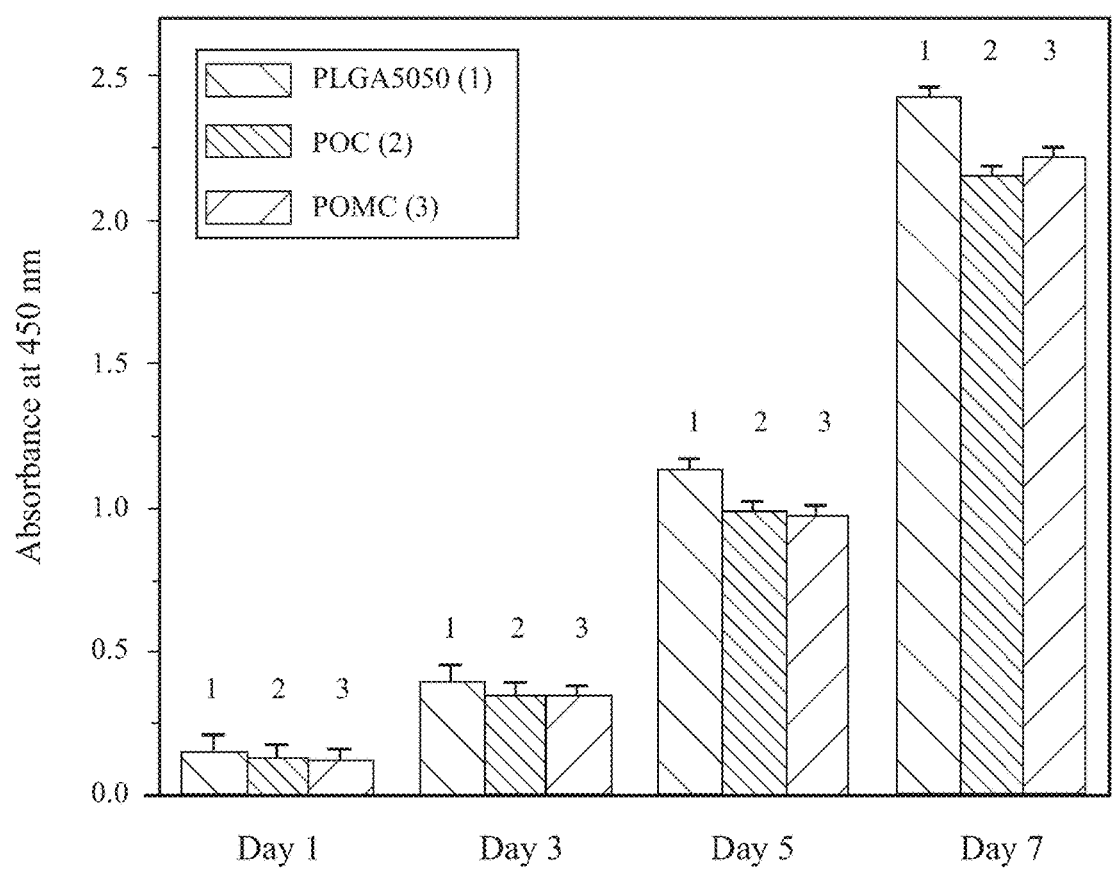
FIG. 8 is a chart showing a CCK8 assay against 3T3 fibroblast to test the cell proliferation on crosslinked POC and POMC films using PLGA5050 film as control.

The polymer films and their degradation products showed minimal cyto-toxicity, as shown in FIGS. 6 and 7, and the polymer films also effectively supported cell proliferation, as shown in FIG. 8.

Given the material characteristics, flexible biodegradable step-index optical fibers may be prepared by the use of POMC as the core material and POC as the cladding material.

Fabrication Method of Citrate-Based Fibers

A two-step fabrication method was developed to achieve the core-cladding bilayer structure 112. The schematic diagram of the fabrication process is shown in FIG. 2a. In Step 1, a coating layer 104 was prepared by using a surface-polished stainless steel wire 102 with a diameter of 500 µm as the mold. Liquid POC pre-polymer is then coated on the surface of the metal wire 102 and then the polymer is thermally crosslinked at 70° C. for 4 days. After the crosslinking, the coating layer 104 turned into the POC cladding tube 106. In order to detach the POC cladding tube 106 from the wire, the polymer-coated wire was immersed in 30% ethanol solution overnight, and the POC tube 106 was then removed from the metal wire 102 due to slight swelling in ethanol. In Step 2, for the preparation of fiber core, an air pressure pump was used to infiltrate POMC pre-polymer 108 into the fabricated cladding tube 106. After thermal crosslinking at 70° C. for 3 days followed by 3 days at 80° C., the POC cladding/POMC core 110/108 were seamlessly grown together and a step-index polymer fiber 112 was obtained.

The method used was suitable for laboratory tests and the invention is not limited to this process. Those of skill in the art will recognize alternatives for larger scale productions.

Structure of Citrate-Based Fibers

Still referring to FIG. 2a, the polymer fiber 112 is schematically shown. The polymer fiber 112 generally includes a core portion 108 and a cladding portion 110. The core portion 108 is positioned within the cladding portion 110. The core portion 108 and the cladding portion 110 are generally concentric.

The preferred diameter of the core is 1 µm-1 mm, and the preferred diameter of the cladding can be from 10 um to 2 mm. The ranges can be adjusted if needed. In some embodiments, multiple cores and multi-layered claddings may be used.

FIG. 9 provides an example showing a fiber 900 having multiple layers of cladding. In one version, the fiber 900 includes a core 902 and multiple cladding layers 904, 906 and 908. In another version, the fiber may include an open channel 902, a core 904 and cladding layers 906 and 908. The open channel 902 may be a microfluidic channel incorporated for delivery or collection of liquids.

Figure 10:
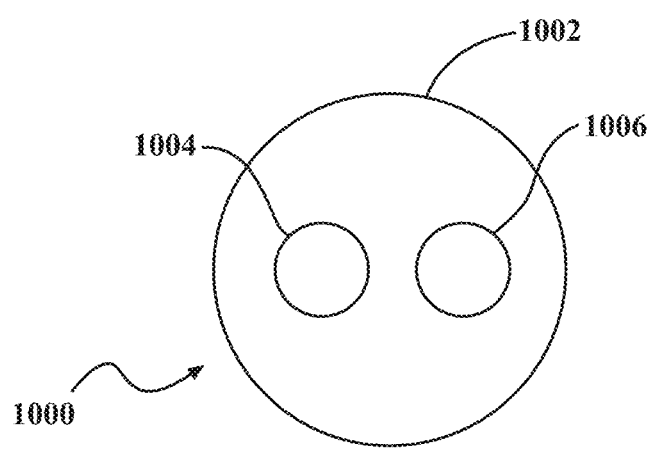
FIG. 10 is a schematic showing an embodiment having two cores.

In another embodiment, as shown in FIG. 10, a fiber 1000 may include more than one core 1004 and 1006 and a cladding layer 1002.

Characterization of Citrate-Based Fibers

Figure 2C:
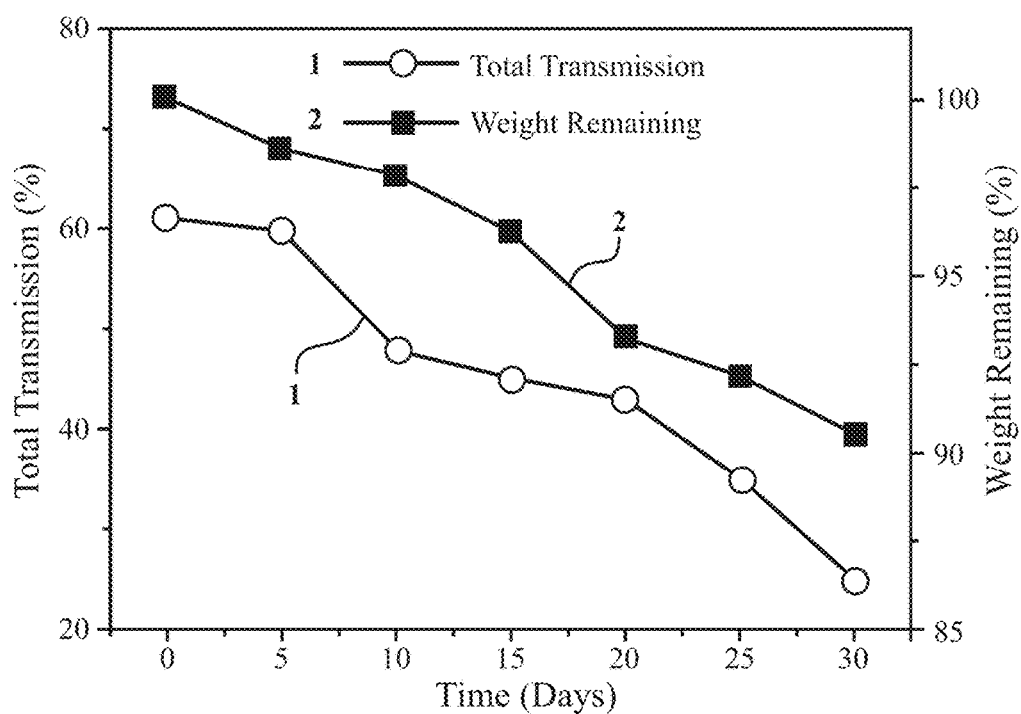
FIG. 2C is a graph showing light transmission changes with fiber degradation.
Figure 2D:
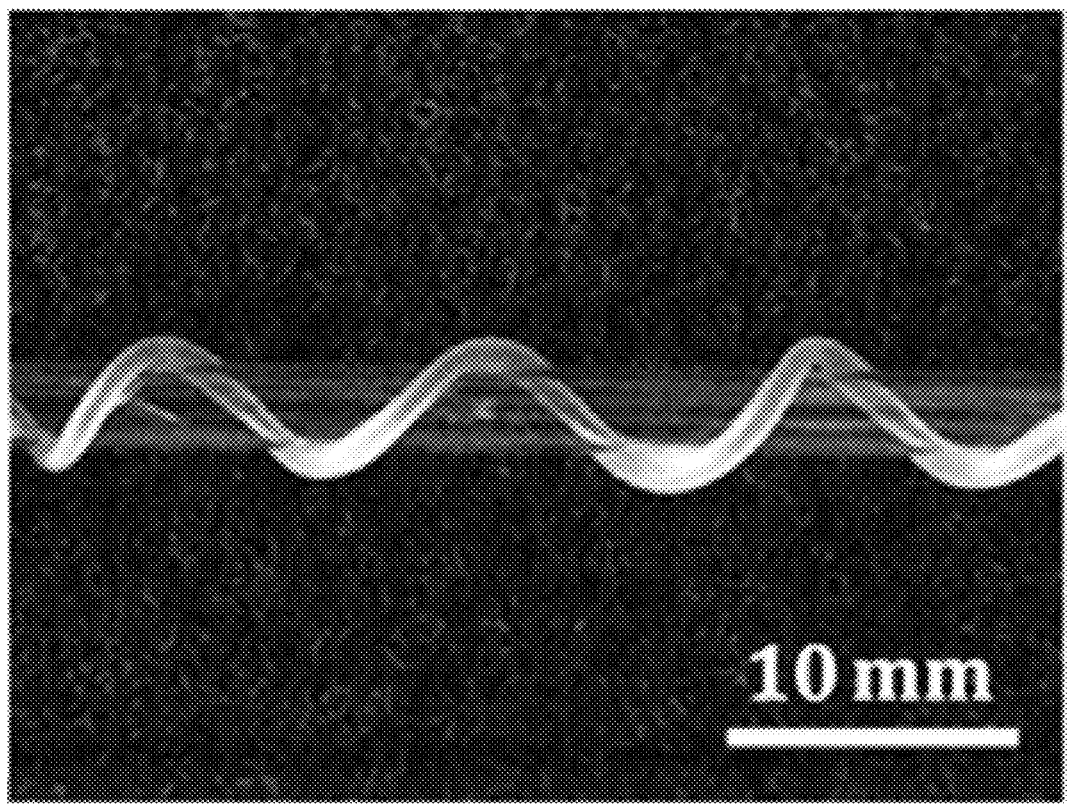
FIG. 2D is a photograph of a citrate-based fiber twisted around a glass tube.
Figure 2E:
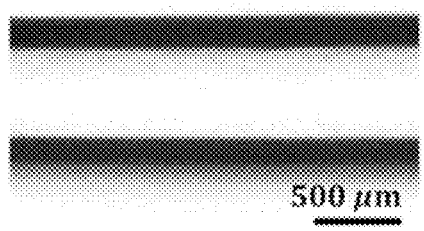
FIG. 2E is a side-view image of a citrate-based fiber under a microscope.
Figure 2F:
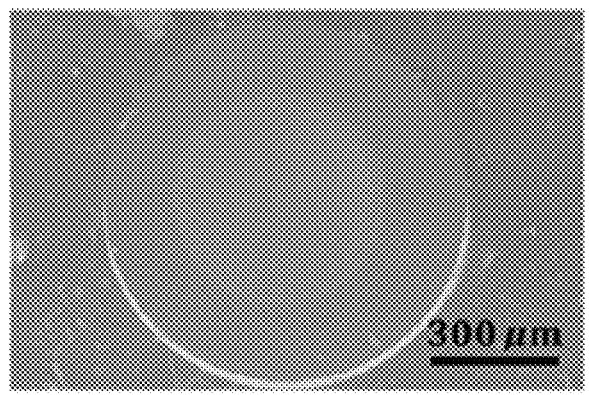
FIG. 2F is a scanning electron microscopy image of a radial cross section of a citrate-based fiber.

The fabricated polymer fiber was mechanically flexible and the fiber can be easily twisted around a glass tube as shown in FIG. 2D. Their favorable elastomeric properties were supported by the classical stress-strain characteristics of elastomeric materials with an initial modulus of 3.39±0.31 MPa, a tensile strength of 1.31±0.25 MPa, and an elongation of 61.49±5.81%, which are consistent with the mechanical properties of individual POC and POMC polymer films, as shown in FIG. 2B. Therefore, the mechanical flexibility of the optical fiber makes it suitable for in vivo biomedical applications. The side view of a fiber under an optical microscope (Nikon, Eclipse, Ti-U) is presented in FIG. 2E, showing the core/cladding structure. Additionally, fibers can be simply cut using normal razor blades; the resulting cross section captured by scanning electron microscopy (SEM) in FIG. 2E shows a smooth facet suitable for optical coupling.

Light Transmission Characterization of Citrate-Based Fibers

Figure 2G:
FIG. 2G is a photograph of a citrate-based fiber showing light guidance by the fiber.

In order to examine the optical performance of the fiber, we coupled light from a 633 nm HeNe laser into the citrate-based fiber to test the wave guiding effect. The sample fiber was mounted on a V-groove and locked by using plasticine. A 88.3-mm focal length lens was chosen to couple light into the fiber to match the numerical aperture. At the output end, a 10× objective was used to collimate the output light from the fiber. The transmission efficiency was calculated based on laser power before and after fiber with loss from optics removed. The light guiding property of the fiber was demonstrated showing successful light delivery, as shown in FIG. 2G. The total transmission of the fiber was measured not only at dry condition, but also at wet condition that the fiber may experience in vivo. Under both conditions, the tested 3-cm-long fiber was able to yield~58% transmission. The laser light was confined inside the core region. During the measurement, the fiber was physically surrounded by plasticine. Yet, light transmission was not affected in spite of the contact between the fiber and the plasticine, supporting the concept that a step index fiber may achieve efficient light transmission in the fiber core due to the intrinsic cladding layer that shields the optical field from the surrounding tissues when used for in vivo applications. The propagation loss of the fiber was determined using a cut-back method. An average propagation loss of 0.4 db/cm was measured. The additional loss compared with the material absorption is introduced by the surface roughness of the metal wire mold and fabrication defects, which can be improved by using a smoother mold and optimized fabrication procedures. The 1/e penetration depth of our fiber is over 10 cm, thus suitable for in vivo experiments.

In vitro degradation studies were also performed on the fibers in phosphate-buffered saline (PBS), which showed that the fibers gradually degraded and reached a weight loss of 9.5% after one month, as shown in FIG. 2C. During the period, optical transmissions were also monitored. The results in FIG. 2C indicate that light transmission was reduced from 60% to 25% after degradation for one month. The decrease of light transmission might be resulted from the defects formed at the core/cladding interface during degradation.

Imaging Through the Citrate-Based Polymeric Fiber

Figure 3A:
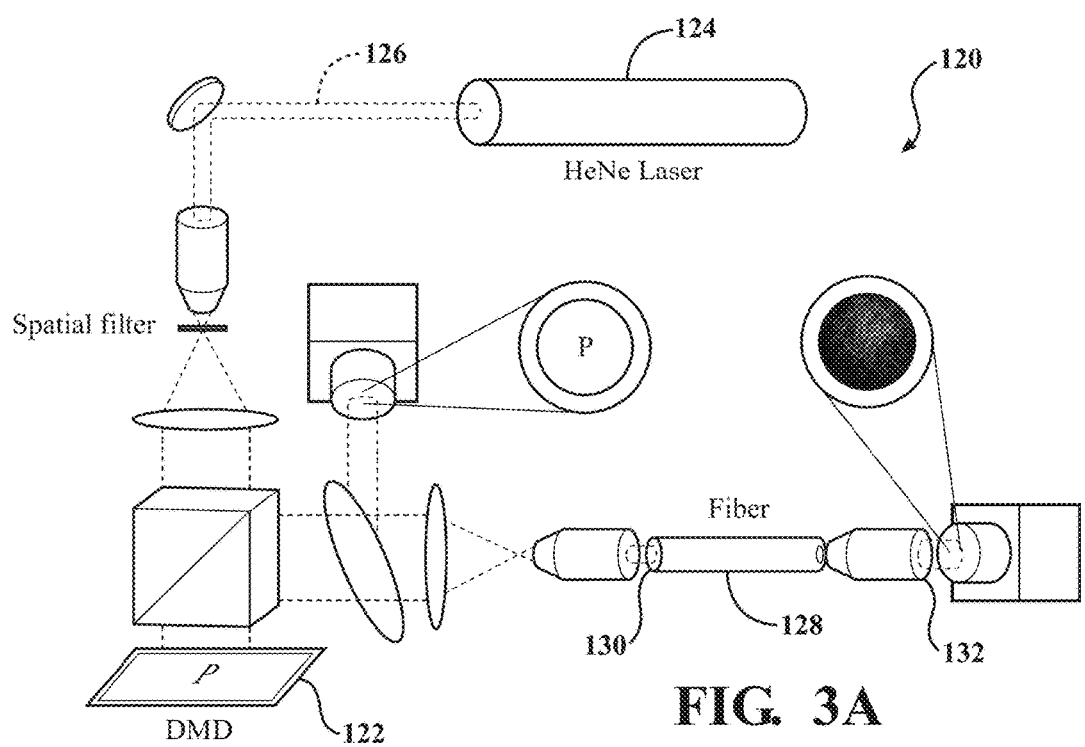
FIG. 3A is a schematic diagram of a experiment setup of the citrate-based polymeric fiber imaging.

The unique optical and mechanical characteristics coupled with programmable degradation capability of the present fibers lend themselves to both in vitro and in vivo bio-sensing and imaging applications. The schematic diagram of the experimental setup 120 is shown by FIG. 3A. A digital micromirror array (DMD) 122 (Texas instruments Discovery 1100) illuminated by a He—Ne laser 124 beam 126 was used to project spatial patterns onto the proximal end 130 of a fiber 128. The corresponding output pattern at the distal end 132 of the fiber was recorded by using a charge-coupled device (CCD) camera. Due to the multi-modal propagation, the output of the fiber contained random speckle patterns, which did not resemble the input image at all. In order to retrieve the images, a least square retrieval algorithm and pre-calibrated impulse response of the fiber were used to reconstruct the input spatial pattern.

To perform imaging using the citrate-based fiber, calibration of the system response was needed. Individual pixels were projected at the proximal end of the fiber and the corresponding output patterns at the distal end were captured, yielding the intensity impulse response matrix H=[$\vec{h}_1, \vec{h}_2, \ldots \vec{h}_n$] of the system, where the ith column vector ($\vec{h}_i$) of H represents the corresponding output pattern, or the impulse response, of the ith input pixel. For a given input image $\vec{x}$, its output pattern is given by $\vec{m}=H\vec{x}+\vec{n}$, where $\vec{m}$ is the measured pattern and $\vec{n}$ is the coherent noise (speckle) background due to interference among the output fields produced by different pixels of the input. This equation can be approximately inverted using the least square method $\vec{x} \approx (H'H)^{-1}H'\vec{m}$. Experimentally, each input pixel (hereafter called super pixel) was comprised of 100 physical pixels (10×10) of the DMD. Since the DMD had a pixel size of 13.68 μm, the actual super pixel size at the fiber end after the telescope system was approximately 9×9 μm$^2$. A total of 64 super pixels (8×8) were used during the experiment to generated input images. Output images at the distal end were recorded by a charge-coupled device camera (480 by 720 pixels), with only the core area of the fiber retained in all recorded images. The impulse response M of the system was a 90000 by 64 matrix, where 90000 is the number of pixels in an output pattern and 64 is the number of available super pixels at the input end. Once the impulse response matrix was measured, a projected input can be reconstructed from its output image.

Figure 3B:
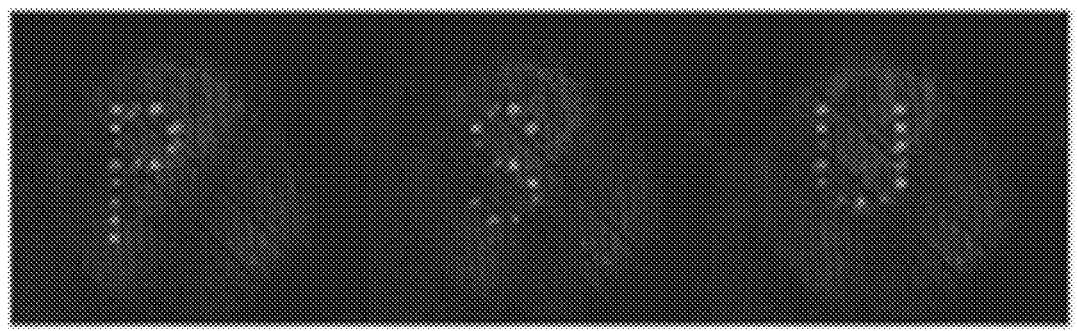
FIG. 3B is a projection image at the proximal end (input end) of the citrate-based polymeric fiber.
Figure 3C:
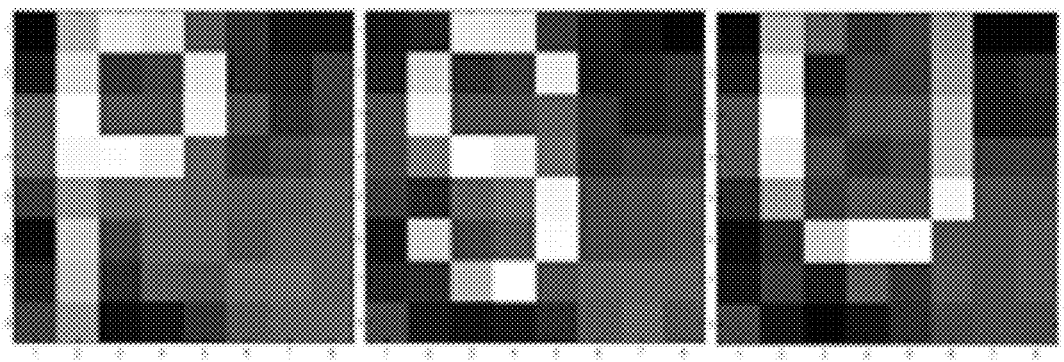
FIG. 3C is reconstructed images.

The experimental result is shown by FIGS. 3B and 3C. The three letters (P, S, and U), initially projected at the proximal end of the fiber is shown in FIG. 3B. The corresponding output at the distal end would be random speckle patterns. By using the pre-recorded impulse responses, the input pattern is retrieved, shown in FIG. 3C, demonstrating the capability of the citrate-based fiber to deliver spatial images.

Deep Tissue Light Delivery

Figure 4A:
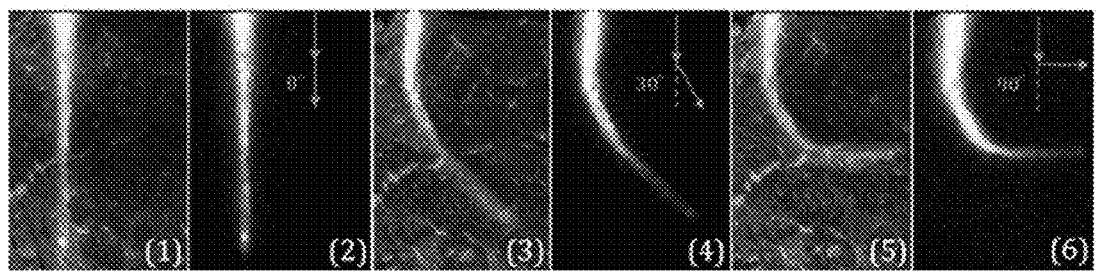
FIG. 4A is a series of photographs showing blue light (473 nm) guidance through a citrate-based polymeric fiber under a thin porcine tissue slice at bending angles of (1, 2) 0, (3, 4) 30 and (5, 6) 90 degrees; b)
Figure 4B:
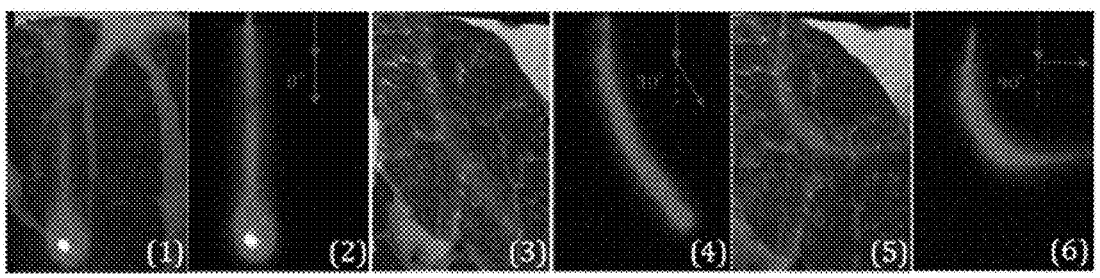
FIG. 4B a series of photographs showing red light (633 nm) delivery through fiber under a thin porcine tissue slice at bending angles of (1, 2) 0, (3, 4) 30 and (5, 6) 90 degrees.

To confirm the practicality for light guiding in tissues, a fiber was placed under a piece of thin porcine tissue slice with a thickness of ~2 mm for study, as shown in FIGS. 4A and 4B. In FIG. 4A, a 473 nm diode-pumped solid-state laser was coupled into the fiber, and the blue light transmits efficiently along the fiber under different bending angles of 0, 30 and 90 degrees, which can be verified by the observation of a bright spot at the distal end of the fiber. In FIG. 4B, the testing based on a 633 nm HeNe laser was also conducted on the fiber, and the fiber shows good light guiding effects for the red light as well. The above studies suggest that the citrate-based polymeric fiber has the ability to guide lights under different wavelengths in tissues, which enables in vivo detection and sensing.

In Vivo Fluorescence Detection

To study the feasibility of using citrate-based fibers for in vivo deep tissue detection and bio-sensing, we performed fluorescence detection experiments with an animal study on a Sprague Dawley (SD) rat and tested our fiber's capability to collect signal underneath deep tissues.

Figure 4C:
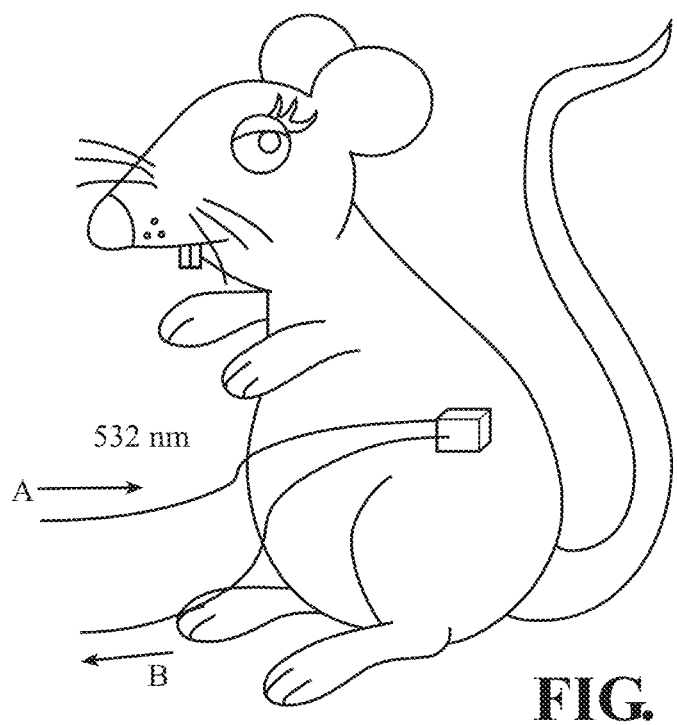
FIG. 4C is a schematic illustration of in vivo deep tissue fluorescence detection with fibers.
Figure 4D:
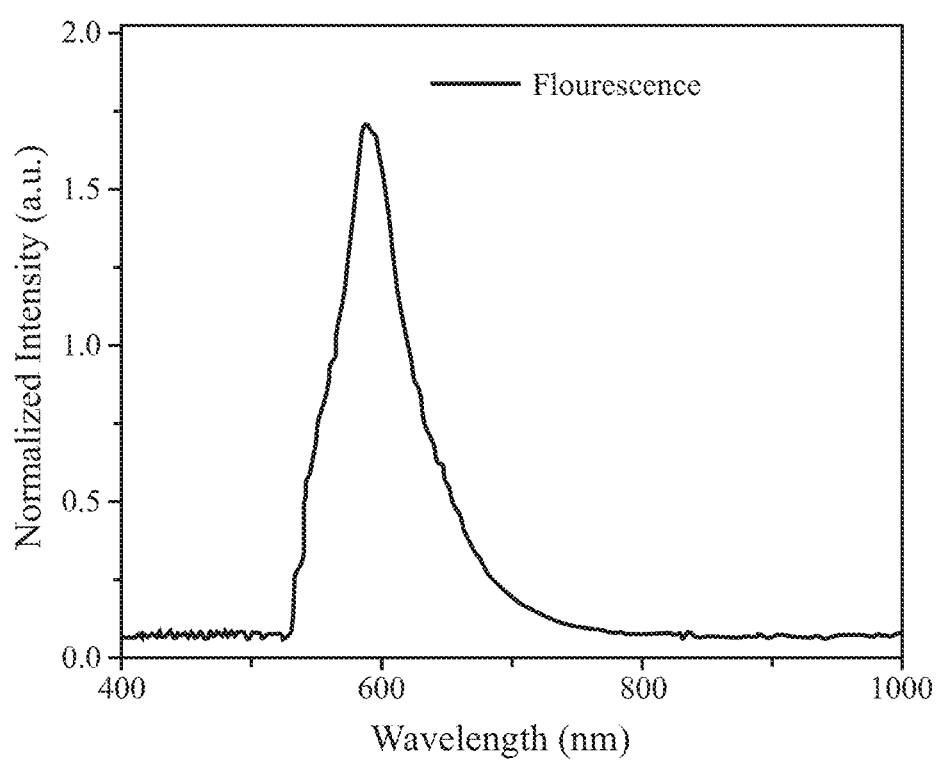
FIG. 4D is the fluorescence spectrum collected from the end of the light collection fiber B.

The experimental procedures are depicted in FIG. 4C. A 16-week-old Sprague Dawley (SD) rat was euthanized with carbon dioxide ($CO_2$) for in vivo experiment. A 20 mW 532 nm laser light was used in the optical setup for deep tissue fluorescence detection study. The Rhodamine B agar gel was placed deep inside the belly area of the SD rats to serve as the fluorescence source, while two citrate-based fibers with a length of 7 cm were used for excitation light delivery and fluorescence collection: Fiber A delivering excitation light from the light source to the Rhodamine B gel, and fiber B collecting the fluorescence emission signal from the gel. At the end of the fiber B, a digital camera was placed to capture fluorescence images, and an Ocean Optics Flame-S spectrometer was used to measure the fluorescence spectrum. The excitation laser light at a wavelength of 532 nm was delivered by the delivery fiber A to illuminate the dyed gel. Emitted red fluorescent light was then detected at the output end of the collection fiber B; a long-pass filter (Chroma ET5421p) was used to block the scattered excitation light. The fluorescence spectrum, as shown in FIG. 4D, accurately matched with the fluorescence spectrum of the original Rhodamine B gel. The in vivo study confirmed efficient organ scale detection capability of the proposed fiber, and demonstrated its mechanical flexibility and feasibility to be implanted inside body without damaging surrounding tissues.

CONCLUSION

In summary, flexible biodegradable step index fibers using designable citrate-based elastomeric polymers through a two-step fabrication method is developed. The obtained step index fiber presented favorable biodegradability and mechanical flexibility. A 0.4 dB/cm loss allowed us to perform both in vitro and in vivo studies inside deep tissue, which showed efficient light transmission and optical signal detection abilities. A preliminary imaging experiment also shows the feasibility of using the fiber for deep tissue implantation and continuous monitoring. With our method, the diameters of core materials and the lengths of fibers can be varied by changing the size of the wire mold. The refractive indices and mechanical properties of core and cladding materials can be further tailored by modifying chemical structures of the citrate-based platform polymers, which allow seamless integration of the core and the cladding. Further, the reactive side groups in citrate-based polymers provide rich opportunities to conjugate functional chemicals, drugs, or biological molecules, and hence fibers with special functionalities, including sensing and potentially disease treatment such as drug delivery, could be designed in the future.

As will be clear to those of skill in the art, the embodiments of the present invention illustrated and discussed herein may be altered in various ways without departing from the scope or teaching of the present invention. Also, elements and aspects of one embodiment may be combined with elements and aspects of another embodiment. It is the following claims, including all equivalents, which define the scope of the invention.

The invention claimed is:

1. A biocompatible and biodegradable polymeric step-index optical fiber, comprising:
    at least one core made from at least one core material, the at least one core material comprising a first polymeric material having a citric acid bonded with at least a first monomer, the core having an initial modulus and a biodegradation rate; and
    at least one cladding around the at least one core, the at least one cladding made from at least one cladding material, the at least one cladding material comprising a second polymeric material having the citric acid bonded with at least a second monomer, the at least second monomer being different from the at least first monomer, the cladding having an initial modulus and a biodegradation rate;
    wherein the core has a refractive index higher than that of the cladding;
    wherein a difference between the initial modulus of the core and the cladding is less than a predetermined threshold and a difference between the biodegradation rates of the core and cladding is less than a predetermined threshold;
    wherein optical properties of the core and cladding are tunable by adjusting monomer ratios, choices of monomers or cross-linking degrees,
    wherein the core material and the cladding material is fabricated by a synthesis process comprising reacting the citric acid with diols and/or amino acids via a facile polycondensation reaction.

2. The biocompatible and biodegradable polymeric step-index optical fiber of claim 1, wherein the difference between the initial modulus of the core and the cladding is less than 30%.

3. The biocompatible and biodegradable polymeric step-index optical fiber of claim 1, wherein the difference between the biodegradation rates of the core and cladding is less than 30% after about 4 weeks.

4. The biocompatible and biodegradable polymeric step-index optical fiber of claim 1, wherein the core material further comprises a third monomer and the cladding material further includes a fourth monomer, and wherein the fourth monomer is the same as or different from the third monomer.

5. The biocompatible and biodegradable polymeric step-index optical fiber of claim 4, wherein the third and/or the fourth monomer is the same as or different from the first or the second monomer.

6. The biocompatible and biodegradable polymeric step-index optical fiber of claim 1, wherein at least one microfluidic channel is incorporated for delivery or collection of liquids.

7. The biocompatible and biodegradable polymeric step-index optical fiber of claim 1, wherein at least one hollow channel is incorporated.

8. The biocompatible and biodegradable polymeric step-index optical fiber of claim 1, wherein more than one core are incorporated.

9. The biocompatible and biodegradable polymeric step-index optical fiber of claim 1, wherein more than one cladding layer is incorporated.

10. The biocompatible and biodegradable polymeric step-index optical fiber of claim 1, wherein the tunable optical properties include the refractive indices of the core and cladding.

11. The biocompatible and biodegradable polymeric step-index optical fiber of claim 1, wherein the refractive index difference between the core and cladding is in the range of $10^{-3}$ to $10^{-1}$.

12. The biocompatible and biodegradable polymeric step-index optical fiber of claim 1, wherein the initial modulus of the core and cladding are in the ranges of $10^{-1}$ to $10^2$ MPa.

13. The biocompatible and biodegradable polymeric step-index optical fiber of claim 1, wherein the tunable optical properties include optical loss, optical gain, light absorption and light emission.

14. The biocompatible and biodegradable polymeric step-index optical fiber of claim 1, wherein the core and/or cladding materials comprise the polymeric material of the respective core and/or cladding conjugated with functional chemicals, biological molecules or drugs such that the core and/or cladding provide adhesive or fluorescent properties.

15. A biocompatible and biodegradable polymeric step-index optical fiber, comprising:
    at least one core made from at least one core material, the at least one core material comprising a first polymeric material having a citric acid bonded with at least a first monomer, the core having an initial modulus and a biodegradation rate; and
    at least one cladding around the at least one core, the at least one cladding made from at least one cladding material, the at least one cladding material comprising a second polymeric material having the citric acid bonded with at least a second monomer, the at least second monomer being different from the at least first monomer, the cladding having an initial modulus and a biodegradation rate;
    wherein the core has a refractive index higher than that of the cladding;
    wherein a difference between the initial modulus of the core and the cladding is less than a predetermined threshold and a difference between the biodegradation rates of the core and cladding is less than a predetermined threshold; and
    wherein optical properties of the core and cladding are tunable by adjusting monomer ratios, choices of monomers or cross-linking degrees,
    wherein the cladding is poly(octamethylene citrate) (POC) and the core is poly(octamethylene maleate citrate) (POMC).

16. The biocompatible and biodegradable polymeric step-index optical fiber of claim 15, wherein:
    a POC pre-polymer is prepared by adding citric acid and 1,8-octanediol (OD) with a molar ratio; and
    a POMC pre-polymer is prepared with a mixture of the citric acid, maleic anhydride, and OD with a molar ratio by replacing part of the citric acid with the maleic anhydride during the synthesis process.

17. The biocompatible and biodegradable polymeric step-index optical fiber of claim 16, wherein the molar ratio of the citric acid and OD is 1:1 for preparing the POC pre-polymer.

18. The biocompatible and biodegradable polymeric step-index optical fiber of claim 16, wherein the molar ratio of the citric acid, maleic anhydride and OD is 0.4:0.6:1 for preparing the POMC pre-polymer.

19. A method of making a biocompatible and biodegradable polymeric step-index optical fiber, the method comprising the steps of:
    providing a first pre-polymer material having a citric acid bonded with at least a first monomer, the core material;

providing a second pre-polymer material having the citric acid bonded with at least a second monomer, the second monomer being different from the first monomer;

providing a surface-polished cylindrical mold;

coating the cylindrical mold with the second pre-polymer material and crosslinking the coated second pre-polymer;

removing the cylindrical mold by swelling the coating to form a cladding; and injecting the first pre-polymer into the cladding and crosslinking the first pre-polymer to form a core;

wherein the core has a refractive index higher than that of the cladding;

wherein a difference between the initial modulus of the core and the cladding is less than 30% and a difference between the biodegradation rates of the core and cladding is less than 30% after about 4 weeks; and wherein optical properties of the core and cladding are tunable by adjusting monomer ratios, choices of monomers or cross-linking degrees.

* * * * *